(12) United States Patent
Dijkstra et al.

(10) Patent No.: US 12,343,061 B2
(45) Date of Patent: Jul. 1, 2025

(54) ELECTROSURGICAL GENERATOR

(71) Applicant: OLYMPUS WINTER & IBE GMBH, Hamburg (DE)

(72) Inventors: Jelle Dijkstra, Berlin (DE); Stefan Schiddel, Stahnsdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 749 days.

(21) Appl. No.: 17/549,041

(22) Filed: Dec. 13, 2021

(65) Prior Publication Data

US 2022/0192726 A1    Jun. 23, 2022

(30) Foreign Application Priority Data

Dec. 17, 2020  (DE) .................. 102020134062.1

(51) Int. Cl.
*A61B 18/12*    (2006.01)
*H01F 27/28*    (2006.01)
*H01F 38/20*    (2006.01)

(52) U.S. Cl.
CPC ......... *A61B 18/1206* (2013.01); *H01F 27/28* (2013.01); *H01F 38/20* (2013.01); *A61B 2018/1286* (2013.01)

(58) Field of Classification Search
CPC ...... A61B 18/1206; A61B 2018/00607; A61B 2018/00625; A61B 2018/1286; H01F 27/28; H01F 38/20
See application file for complete search history.

(56) References Cited

U.S. PATENT DOCUMENTS

| | | | |
|---|---|---|---|
| 4,739,759 A | | 4/1988 | Rexroth et al. |
| 2009/0318915 A1 | * | 12/2009 | Hosier ............... A61B 18/12 606/33 |
| 2014/0074084 A1 | * | 3/2014 | Engeberg ........... A61B 18/1445 606/33 |
| 2020/0395158 A1 | | 12/2020 | Kim et al. |

FOREIGN PATENT DOCUMENTS

| | | |
|---|---|---|
| CN | 112071595 A | 12/2020 |
| DE | 614728 C | 6/1935 |
| DE | 69221942 T2 | 3/1998 |
| DE | 60302409 T2 | 8/2006 |
| DE | 11 2009 001 250 T5 | 4/2011 |
| EP | 0517243 A1 | 12/1992 |
| EP | 1402838 A1 | 3/2004 |

OTHER PUBLICATIONS

May 12, 2022 Extended Search Report issued in European Patent Application No. 21214533.8.
Oct. 8, 2021 Office Action issued in German Patent Application No. 10 2020 134 062.1.

* cited by examiner

*Primary Examiner* — Tigist S Demie
(74) *Attorney, Agent, or Firm* — Oliff PLC

(57) ABSTRACT

An electrosurgical generator for providing different high-frequency alternating voltages/high-frequency alternating currents includes at least two outputs to which an electrosurgical instrument is or can be connected, at least one high-frequency voltage source, and at least two output transformers connected on the primary side to the high-frequency voltage source and on the secondary side to the outputs for an electrosurgical instrument, wherein both the primary windings of the output transformers can be interconnected via switches and the secondary windings of the output transformers can be interconnected via switches.

13 Claims, 7 Drawing Sheets

ELECTROSURGICAL GENERATOR

Figure 1:
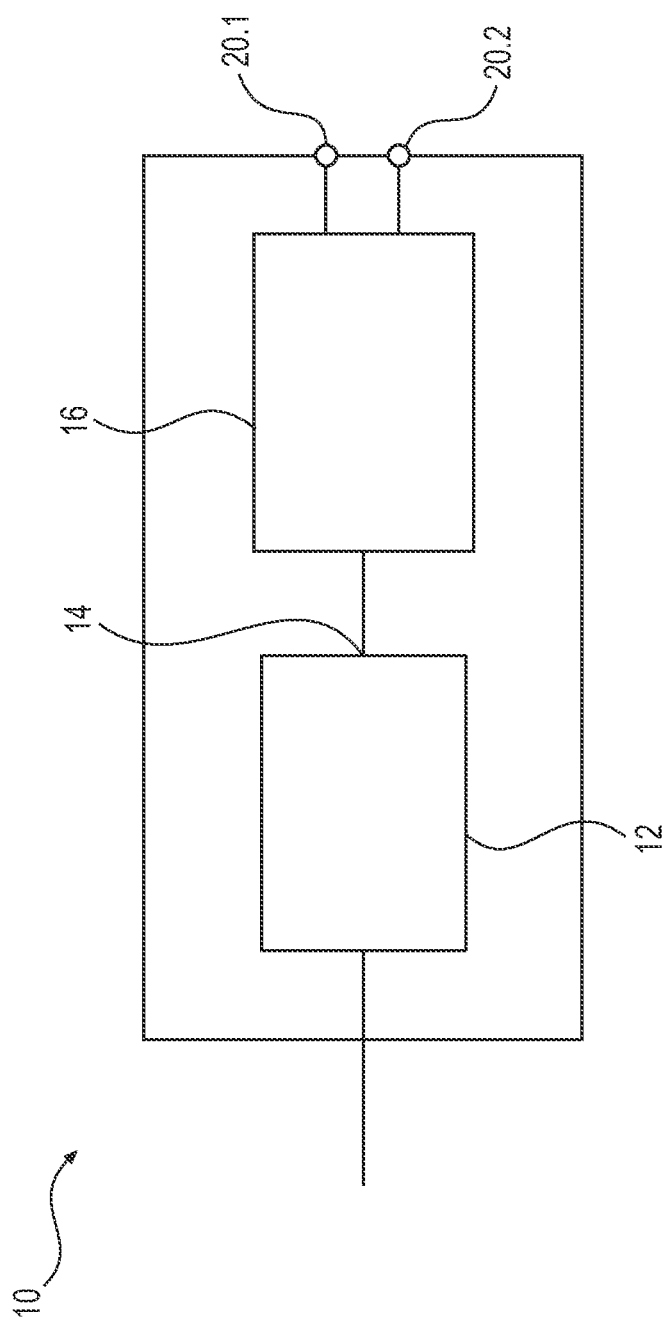

The invention relates to an electrosurgical generator for providing a high-frequency alternating current/a high-frequency alternating voltage, comprising at least two outputs to which an electrosurgical instrument is or can be connected, at least one high-frequency voltage source, and at least two output transformers connected on the primary side to the high-frequency voltage source and on the secondary side to the outputs for an electrosurgical instrument.

Electrosurgery can be used for cutting, coagulating (obliterating) and/or vaporizing biological tissue, i.e. body tissue. For this purpose, a high-frequency alternating voltage/current is usually directed into the body tissue via an electrosurgical instrument, with the electrosurgical instrument being connected to the outputs of an electrosurgical generator.

Known electrosurgical generators are designed to offer different modes of operation so that one electrosurgical generator can be used to cut, coagulate, as well as vaporize. Depending on the application (cutting, coagulating or vaporizing), certain high-frequency alternating voltages/alternating currents (hereinafter simply referred to as output voltage) are required. In order to be able to provide a specific output voltage, known electrosurgical generators have a high-frequency voltage source that generates a sinusoidal high-frequency voltage (200 kHz-5 MHz) from a DC voltage. The high-frequency voltage source typically includes a voltage source connected to an inverter. In order to provide the required output voltage at the outputs of the electrosurgical generator, which can vary from several volts to several kilovolts depending on the application, an output transformer is also arranged between the high-frequency voltage source and the outputs for an electrosurgical instrument, via which the output voltage is scaled and which also ensures galvanic isolation from the patient circuit.

To cover the required output voltage range, different transformer ratios are required between the high-frequency voltage source and the outputs for an electrosurgical instrument. Various concepts are known to provide multiple transformer ratios within a single electrosurgical generator.

For example, the use of an output transformer having a plurality of secondary windings connected in series is known. The use of an output transformer having a plurality of primary windings connected in series is also known. The disadvantage of these two concepts is that voltages also occur at the open-circuit windings that are not used because they are magnetically coupled to the primary winding. These voltages cause high stress on the dielectric between the windings and can increase the patient leakage currents of the generator. In addition, the transformer would be very complex because of the multiple taps.

According to another concept, an output transformer is provided in an electrosurgical unit for each desired transmission ratio. The disadvantage of this concept is that a lot of space is required in the generator for the different output transformers, although only one transformer is required for the use of an operating mode in each case. Accordingly, the output transformers are not used efficiently.

The task upon which the invention is based is to expand the range of applications of an electrosurgical generator.

According to the invention, it is provided that both the primary windings of the output transformers of the electrosurgical generator can be interconnected via switches and the secondary windings of the output transformers of the electrosurgical generator can be interconnected via switches.

In the present invention, it has been recognized that a useful combination of the concepts known from prior art can be quite advantageous because the use of multiple output transformers in conjunction with switching capabilities that interconnect specified primary windings of the output transformers and/or secondary windings of the output transformers, as needed, provides a simple way to establish different transformer ratios between the high-frequency voltage source and the outputs for an electrosurgical instrument without the disadvantages known from prior art. In addition, the combination according to the invention of at least two output transformers, whose primary and secondary windings can be coupled via switches, results in a transformer combination that behaves outwardly like a single transformer without generating unused open-circuit voltages.

According to a preferred configuration, the variance of the different transformer ratios can be further increased if a coupling of the primary windings and/or the secondary windings of the output transformers via the switches is designed in such a way that the primary windings and the secondary windings can each be optionally connected in parallel and/or in series or operated individually.

According to a further configuration of the invention, at least one output transformer may have at least one tap on the primary and/or secondary side. This configuration allows for further variance in transmission ratios. For example, center taps can be used to operate instruments with more than two electrodes.

The switches are opened and closed via a control unit. The control unit contains or receives, from another control unit, the information when an actuation of the switches should take place. Preferably, the actuation of the switches occurs when an operating mode has been selected and the instrument is put into operation. However, it is also conceivable that the sequence in which the switches must be opened or closed in order to obtain certain transmission ratios has been defined and stored in advance.

In a preferred configuration, the electrosurgical generator according to the invention has three output transformers, each with a different transmission ratio, wherein the center transformer must be "rotated" either primarily or secondarily to obtain the correct arrangement of polarity points of the individual output transformers. The three primary windings of the individual transformers are each connected in series. The three secondary windings of the individual transformers are also each connected in series. At least two switches are provided both on the primary side and on the secondary side, which are connected to the primary windings and the secondary windings, respectively, in such a way that a first switch is used to bridge the first and second primary windings when the first switch is closed;
 a second switch is used to bridge the second and third primary windings when the second switch is closed;
 a third switch is used to bridge the first and second secondary windings when the third switch is closed; and
 a fourth switch is used to bridge the second and third secondary windings when the first switch is closed.

For this purpose, the first switch is connected in parallel to the first and second primary windings. The second switch is connected in parallel to the second and third primary windings. The third switch is connected in parallel to the first and second secondary windings. The fourth switch is connected in parallel to the second and third secondary windings.

Preferably, the electrosurgical generator has a control unit for controlling the four switches. The control unit is designed to provide four different operating modes by respectively opening or closing the switches.

In a first operating mode, the two switches on the primary side are open and all primary windings are connected in series. At the same time, the two switches on the secondary side are closed and the three secondary windings are connected in parallel.

In a second operating mode, the first switch on the primary side, connected in parallel to the first primary winding and the second primary winding, is open, while the second switch on the primary side, connected in parallel to the second and third primary windings, is closed. At the same time, the first switch on the secondary side, connected in parallel to the first and second secondary windings, is open, and the second switch on the secondary side, connected in parallel to the second and third secondary windings, is closed.

In a third operating mode, the first switch on the primary side, connected in parallel to the first primary winding and the second primary winding, is closed, and the second switch on the primary side, connected in parallel to the second and third primary windings, is open. At the same time, the first switch on the secondary side, connected in parallel to the first and second secondary windings, is closed, and the second switch on the secondary side, connected in parallel to the second and third secondary windings, is open.

In a fourth operating mode, the two switches on the primary side are closed and the three primary windings are connected in parallel. At the same time, the two switches on the secondary side are open and the three secondary windings are connected in series.

According to a further advantageous configuration of the invention, the transmission ratios of the two outer output transformers are configured differently. The advantage of this configuration is that these two output transformers can also be switched individually. The transmission ratio of the center output transformer should then be of the same order as the smaller transmission ratio of the two outer output transformers.

To enable activation of two electrosurgical instruments, the electrosurgical generator according to the invention may have at least two high-frequency voltage sources, wherein the voltage sources may be connected to the primary windings of the output transformers via switches.

The switches are preferably designed as relays.

The electrosurgical generator is preferably configured to provide an AC output voltage at its outputs at a frequency between 0.2 MHz and 3 MHz.

The electrosurgical generator is preferably configured to provide an AC output voltage between 20 V and 5 kV at its outputs.

The electrosurgical generator is preferably configured to provide an output power of up to 500 W at its outputs.

The electrosurgical generator is preferably configured to provide operating modes for both cutting and coagulating body tissue.

An electrosurgical generator configured in this manner can be operated universally and economically in conjunction with at least two output transformers that outwards function as a single output transformer.

The invention will now be explained in more detail using an exemplary embodiment and referencing the figures. The figures show the following:

FIG. 1: shows a schematic diagram of some components of an electrosurgical generator for supplying an electrosurgical instrument with high-frequency AC voltage.

Figure 2:
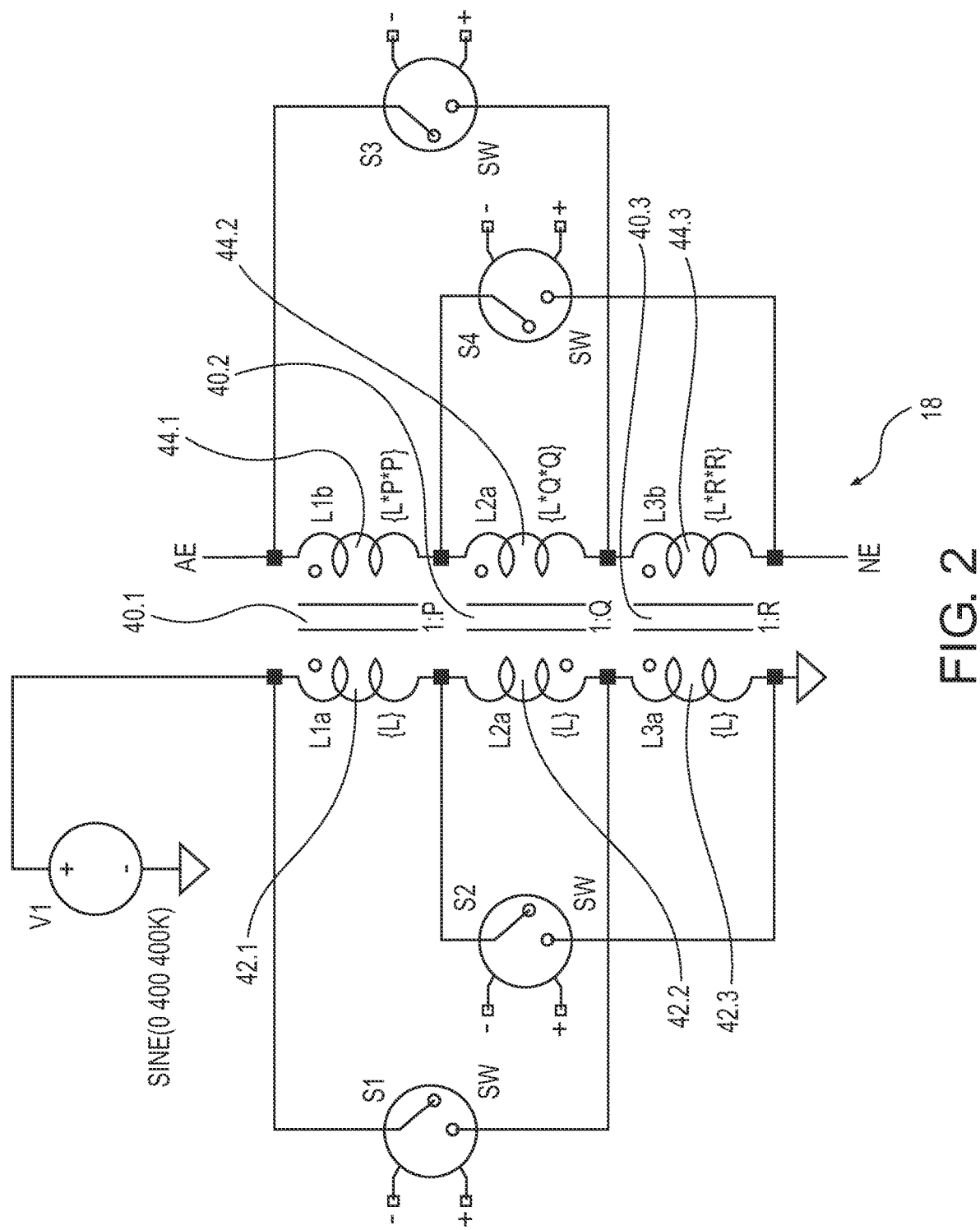

FIG. 2: shows a schematic diagram of a first embodiment of an output transformer, formed by three individual transformers connected in series, of the electrosurgical generator of FIG. 1.

Figure 3:
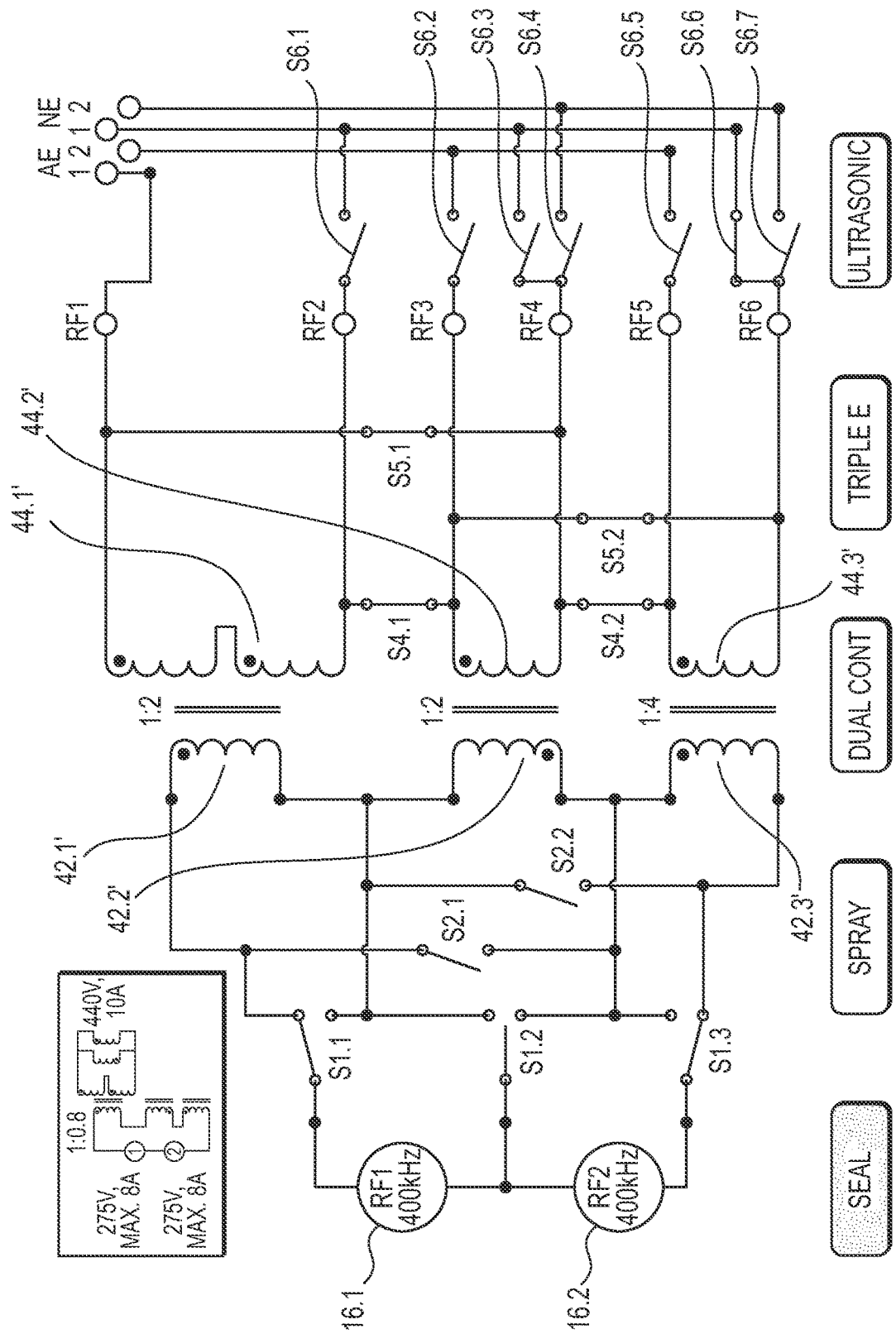

FIG. 3: shows a schematic diagram of a second embodiment of an output transformer, formed by three individual transformers connected in series, in a first operating mode.

Figure 4:
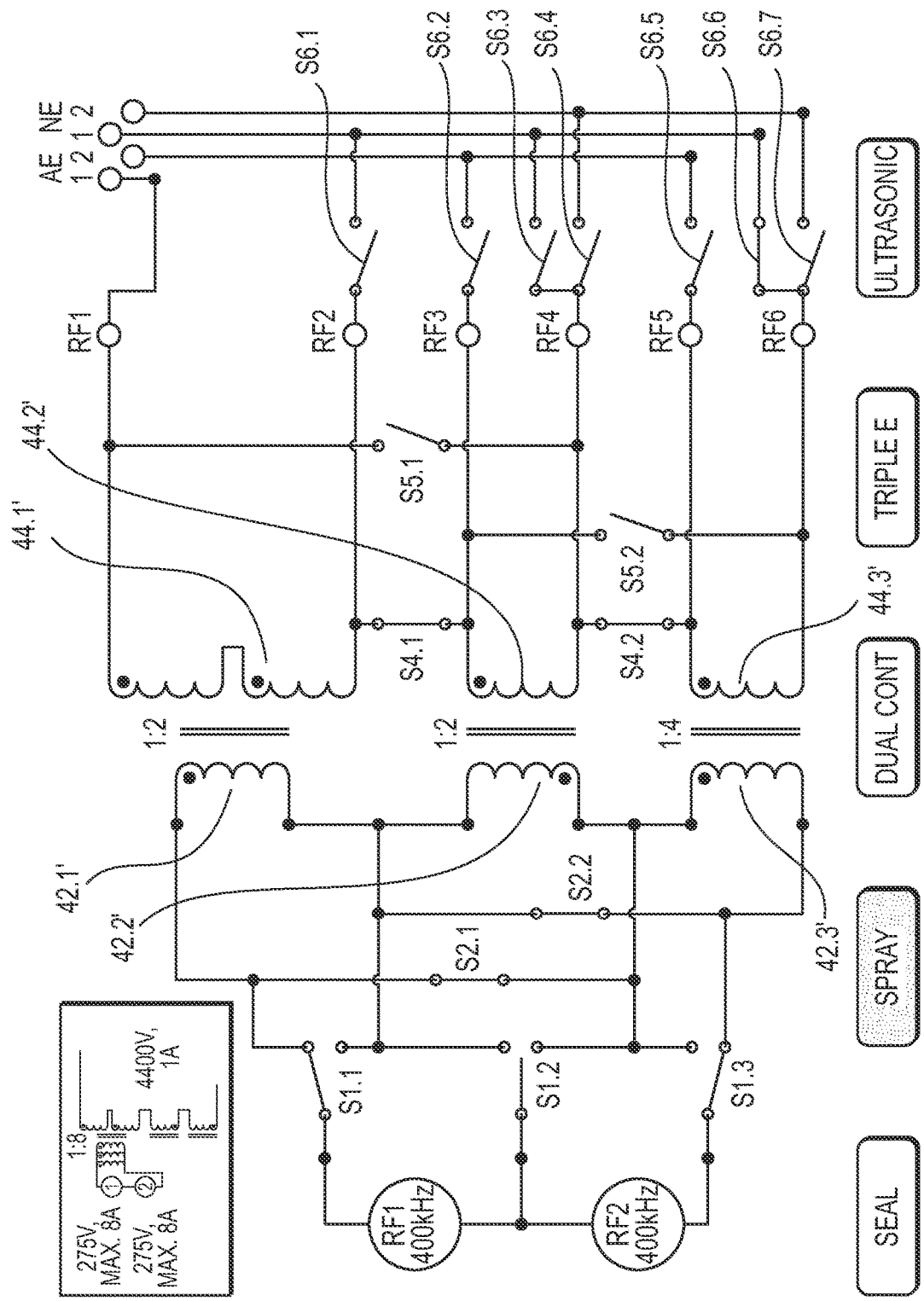

FIG. 4: shows a schematic diagram of a second embodiment of an output transformer, formed by three individual transformers connected in series, in a second operating mode.

Figure 5:
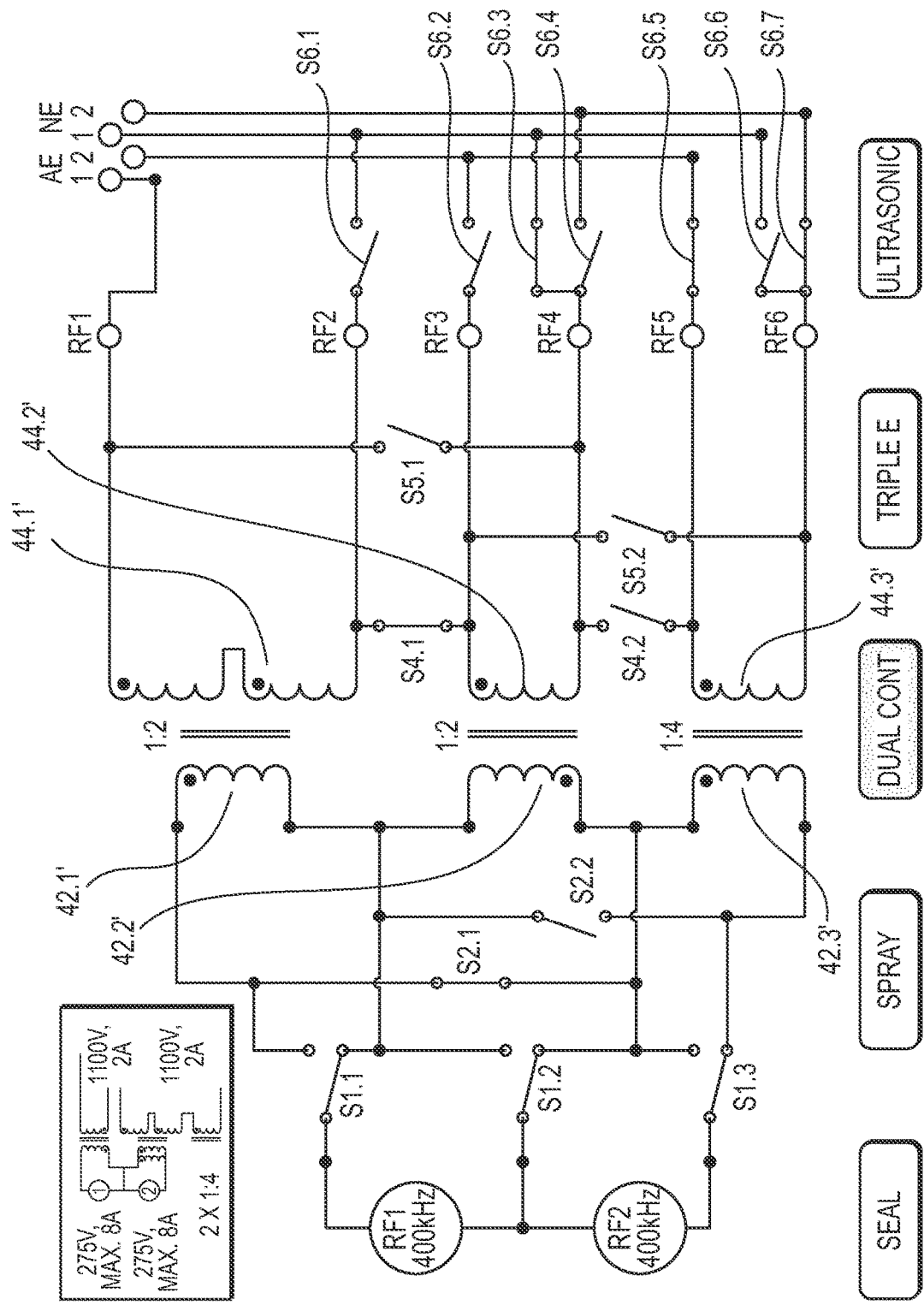

FIG. 5: shows a schematic diagram of a second embodiment of an output transformer, formed by three individual transformers connected in series, in a third operating mode.

Figure 6:
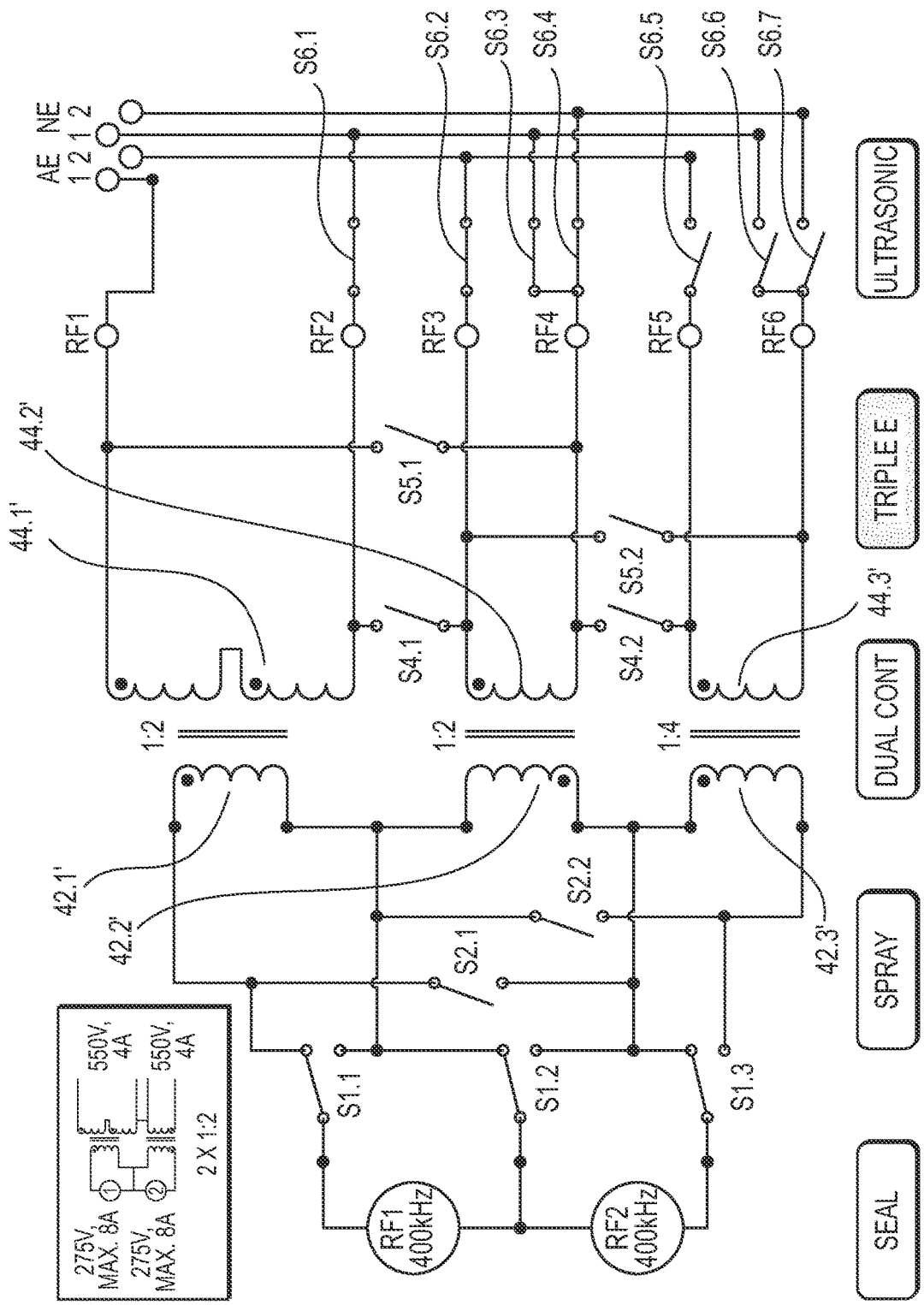

FIG. 6: shows a schematic diagram of a second embodiment of an output transformer, formed by three individual transformers connected in series, in a fourth operating mode.

Figure 7:
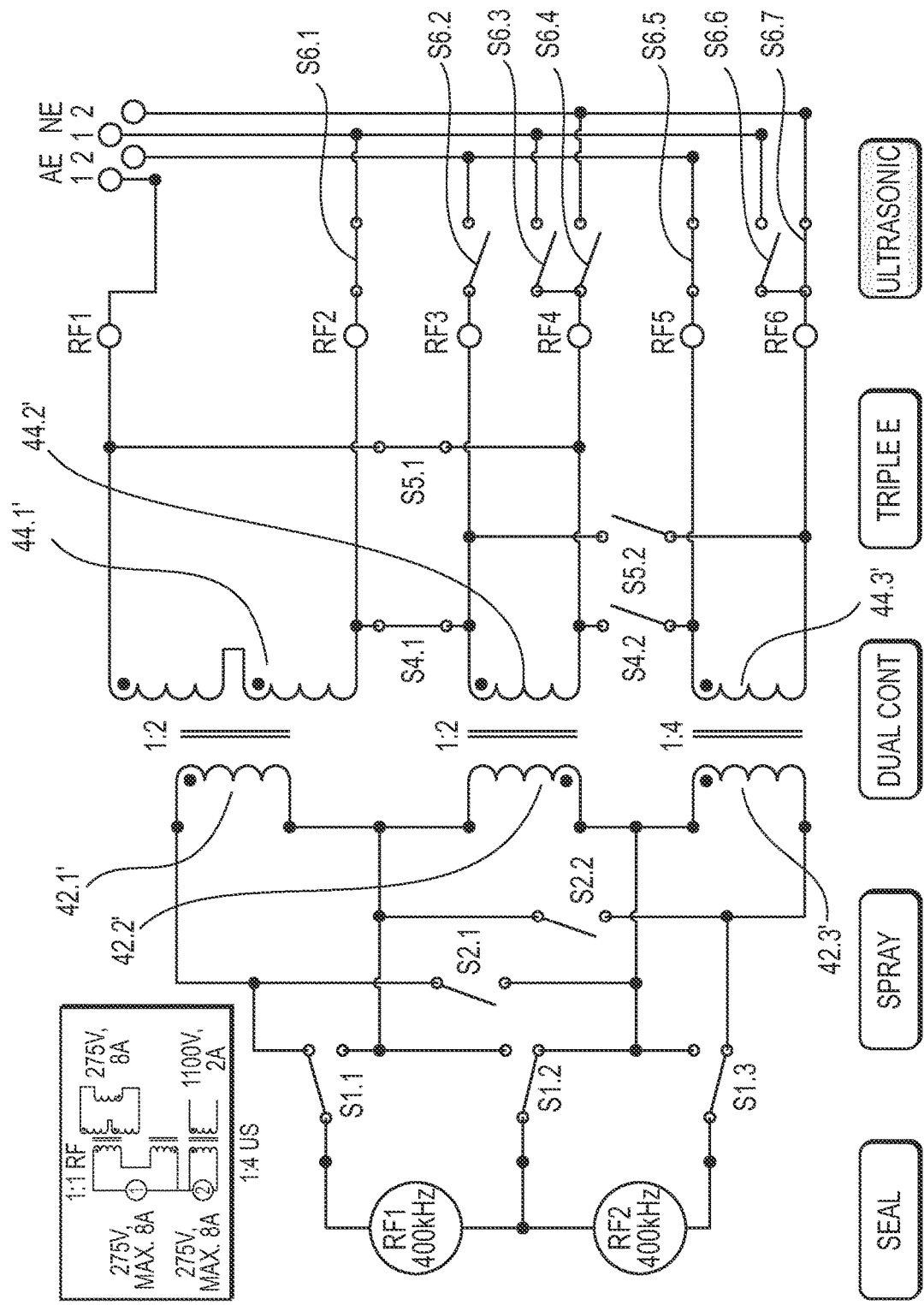

FIG. 7: shows a schematic diagram of a second embodiment of an output transformer, formed by three individual transformers connected in series, in a fifth operating mode.

FIG. 1 shows an example of an electrosurgical generator 10 according to the invention. As can be seen in FIG. 1, the electrosurgical generator 10 features a high-frequency voltage source 12 that can be connected to the public power grid, for example, and provides a DC output voltage at its output 14. The DC output voltage is applied to a high-frequency part 16 of the electrosurgical generator 10. The high-frequency part 16 of the electrosurgical generator 10 serves as an inverter and produces a high-frequency AC output voltage that is supplied to outputs 20.1 and 20.2 of the electrosurgical generator 10. An electrosurgical instrument can be connected to the outputs 20.1 and 20.2 of the electrosurgical generator 10.

For example, the high-frequency part 16 of the electrosurgical generator 10 is designed to output a high-frequency alternating current and a high-frequency alternating voltage having a frequency between 200 kHz and 5 MHz. The desired amplitude of the AC output voltage can vary from a few volts to a few kilovolts and depends on the respective application.

To achieve a wide range of possible output voltages, the electrosurgical generator in the exemplary embodiment shown in FIG. 2 comprises three individual transformers 40.1, 40.2 and 40.3. Each individual transformer 40.1, 40.2 and 40.3 has a primary winding 42.1, 42.2 and 42.3 and a secondary winding 44.1, 44.2 and 44.3. Both the three primary windings 42.1, 42.2, and 42.3 and the three secondary windings 44.1, 44.2, and 44.3 are each connected in series, wherein the center transformer 40.2 was rotated to maintain the correct arrangement of the polarity points of the individual output transformers on the primary side.

Each of the individual transformers 40.1, 40.2 and 40.3 of the exemplary embodiment shown in FIG. 2 has a different transmission ratio. The respective transmission ratio results from the ratio of the number of turns of the respective primary winding to the number of turns of the corresponding secondary winding. Here, the ratio of the input voltage to the output voltage of the respective individual transformer 40.1, 40.2 and 40.3 is inversely proportional to the ratio of the number of turns of the primary winding to the number of turns of the secondary winding. The transmission ratio—this is the ratio of the input voltage to the output voltage of the respective individual transformer—is given for the individual transformers 40.1, 40.2 and 40.3 in FIG. 2 as 1:P, 1:Q and 1:R respectively.

In addition to the three individual transformers 40.1, 40.2 and 40.3, two switches are provided both on the primary side—i.e. on the side of the primary windings 42.1, 42.2 and 42.3—and on the secondary side—i.e. on the side of the secondary windings 44.1, 44.2 and 44.3—each of which can bridge two of the three windings in its closed state. Specifically, a switch 51 is connected in parallel to the primary windings 42.1 and 42.2 and can bridge these two primary windings. A switch S2 is connected in parallel to the primary windings 42.2 and 42.3 and can bridge these two primary windings.

Similarly, two switches S3 and S4 are also provided on the secondary side, of which switch S3 is connected in parallel to the secondary windings 44.1 and 44.2, and switch S4 is connected in parallel to the secondary windings 44.2 and 44.3.

The switches S1 and S2 on the primary side and the switches S3 and S4 on the secondary side can be used to switch between different transmission ratios.

For example, if, in a first operating mode, the two switches S1 and S2 on the primary side are open, all primary windings 42.1, 42.2 and 42.3 are connected in series. If, at the same time, the two switches S3 and S4 on the secondary side are closed, the three secondary windings 44.1, 44.2 and 44.3 are connected in parallel. With switches S1 and S2 on the primary side open and switches S3 and S4 on the secondary side closed, the transmission ratio is 1:(1/P+1/Q+1/R). This is the lowest possible transmission ratio, which also requires the lowest magnetizing current.

In a second operating mode, if the first switch S1 on the primary side, connected in parallel to the two primary windings 42.1 and 42.2, is open while the second switch S2 on the primary side, connected in parallel to the primary windings 42.2 and 42.3, is closed, only the primary winding 44.1 of the first transformer 40.1 is active because the other two primary windings 42.2 and 42.3 are bridged by the second switch S2 on the primary side. If, at the same time, the first switch S3 on the secondary side, which is connected in parallel to the secondary windings 44.1 and 44.2, is open and the second switch S4 on the secondary side, which is connected in parallel to the secondary windings 44.2 and 44.3, is closed, only the first of the secondary windings 44.1 is active on the secondary side because the two remaining secondary windings 44.2 and 44.3 are bridged by switch S4. In this case, the transmission ratio of the output transformer 18 corresponds to the transmission ratio of the first individual transformer 40.1, and accordingly is 1:P.

If, in a third operating mode, the first switch S1 on the primary side is closed and the second switch S2 on the primary side is open, only the third primary winding 44.3 is active on the primary side because the first switch S1 on the primary side bridges the remaining two primary windings 42.1 and 42.2. If, at the same time on the secondary side, the first switch S3 on the secondary side is closed and the second switch S4 on the secondary side is open, only the third secondary winding 44.3 is active on the secondary side because the remaining windings 44.1 and 44.2 on the secondary side are bridged by the second switch S3 on the secondary side. The output transformer 18 then has a transmission ratio of 1:R, which is the transmission ratio of the third individual transformer 40.3.

If, in a fourth operating mode, the two switches S1 and S2 on the primary side are closed, the three primary windings 42.1, 42.2 and 42.3 are connected in parallel. If, at the same time, the two switches S3 and S4 on the secondary side are open, the three secondary windings 44.1, 44.2 and 44.3 are connected in series. In this case, the output transformer 18 has a transmission ratio of 1:(P+Q+R). This is the highest transmission ratio the output transformer 18 can have, resulting in the highest magnetizing current.

The switches S1, S2, S3 and S4 can be relays, for example, but also field-effect transistors, if necessary.

A control unit 46 is provided for controlling the switches S1, S3, S3 and S4. This control unit is configured in such a way that it causes the appropriate switches to open and close for providing the operating modes described herein.

For example, in order to be able to achieve desired transmission ratios of 1:2.6, 1:7.4, and 1:13.4 in practice, the values for P, Q, and R that determine the transmission ratios of the individual transformers 40.1, 40.2, and 40.3 could be selected as follows: P=2.6, R=7.4, and Q=3.4. With these values, the output transformer 18 can also achieve a fourth transmission ratio of 1 to 0.8.

The exemplary embodiment of an electrosurgical generator shown in FIG. 2 can, with appropriate modification, be designed to provide operating modes that allow the simultaneous use of two electrosurgical instruments. A corresponding exemplary embodiment is shown in FIGS. 3 to 7. FIGS. 3 to 7 each show the same output transformer in different configurations for different operating modes, which are implemented by corresponding switch positions of switches of the output transformer. Another difference of the output transformer shown in FIGS. 3 to 7 as compared to the output transformer shown in FIG. 2 is that not only a single pair of outputs 20.1 and 20.2 for connecting a working electrode AE and a neutral electrode NE is provided, but two outputs each for two different working electrodes AE1 and AE2 as well as two different neutral electrodes NE1 and NE2.

Like the exemplary embodiment shown in FIG. 2, the exemplary embodiments shown in FIGS. 3 to 7 also have three individual transformers, each of which has a primary winding 42.1', 42.2' and 42.3' and also a secondary winding 44.1', 44.2' and 44.3'. In the exemplary embodiment of an output transformer shown in FIGS. 3 to 7, the center individual transformer is also inverted with the primary winding 42.2' and with respect to the other two individual transformers.

The primary windings 42.1', 42.2' and 42.3' are connected in series just like the primary windings of the output transformer shown in FIG. 2. The same applies to the secondary windings 44.1', 442.' and 44.3', although in contrast to the exemplary embodiment shown in FIG. 2, switches S4.1 and S4.2 are provided between the individual secondary windings 44.1', 44.2' and 44.3'; these switches can be used to cancel the series connection between the secondary windings 44.1', 44.2' and 44.3'. Specifically, by means of the switch S4.1, the electrical connection between the first secondary winding 44.1' and the second secondary winding 44.2' can be interrupted by opening the switch S4.1. Accordingly, the electrical connection and thus the series connection between the second secondary winding 44.2' and the third secondary winding 44.3' can be interrupted by opening the switch S4.2.

Another difference to the exemplary embodiment shown in FIG. 2 is that, instead of a single high-frequency part 16, two high-frequency parts 16.1 and 16.2 are provided that are connected in series, whereby the use of two high-frequency parts 16.1 and 16.2 results in a center tap. Three switches S1.1, S1.2 and S1.3 connected to the total of three terminals of the high-frequency parts 16.1 and 16.2 connected in series allow for the high-frequency parts 16.1 and 16.2 to be connected either in series or individually to one or more of the primary windings 42.1', 42.2' and 42.3'.

When the switches S1.1, S1.2 and S1.3 are in the switch position shown in FIGS. 3 and 4, the high-frequency parts 16.1 and 16.2 connected in series are connected in parallel to the series connection of the primary windings 42.1', 42.2' and 42.3', so that the series connection of the primary windings 42.1', 42.2' and 42.3' is supplied with voltage by the high-frequency parts 16.1 and 16.2 connected in series in the same way as the primary windings 42.1, 42.2 and 42.3 of the output transformer in FIG. 2 are supplied with voltage by a single high-frequency part. By connecting the high-frequency parts 16.1 and 16.2 in series, these high-frequency parts 16.1 and 16.2 provide a total output voltage equal to the sum of the output voltages of the two individual high-frequency parts 16.1 and 16.2.

If only the output voltage of the high-frequency parts 16.1 and 16.2 connected in series is to be applied to the series connection of the primary windings 42.1', 42.2' and 42.3', the switch S1.2 connected to the center tap between the two high-frequency parts 16.1 and 16.2 can remain fully open, as shown in FIGS. 3 and 4.

If—as shown in FIG. 3—the high-frequency parts 16.1 and 16.2 connected in series are connected in parallel with the series connection of the primary windings 42.1', 42.2' and 42.3' by means of the switches S1.1 and S1.3, and at the same time the switches S2.1 and S2.2 corresponding to the switches S1 and S2 from the exemplary embodiment in FIG. 2 are open, the primary windings 42.1', 42.2' and 42.3' function in series.

If, at the same time, the switches S5.1 and S5.2 for connecting the secondary windings 44.1, 44.2' and 44.3' in parallel are closed, the secondary windings 44.1', 44.2' and 44.3' are connected in parallel. The transmission ratio of the output transformer in the operating mode shown in FIG. 3 then results from the series connection of the primary windings 42.1', 42.2' and 42.3' and the parallel connection of the secondary windings 44.1', 44.2' and 44.3'. If the transmission ratio of the first two individual transformers with their primary windings 42.1' and 42.2' and their secondary windings 44.1' and 44.2' is 1:2 in each case, and the transmission ratio of the third individual transformer with the primary winding 42.3' and the secondary winding 44.3' is 1:4, the total transmission ratio of the exemplary embodiment shown in FIG. 3 with primary windings 42.1', 42.2', 42.3' connected in series and secondary windings 44.1', 44.2' and 44.3' connected in parallel is 1:0.8.

An equivalent circuit diagram is shown in the top left corner of FIG. 3; it illustrates how the output transformers in the exemplary embodiment shown in FIG. 3 are configured based on the respective switch positions as a result.

The output transformer configuration shown in FIG. 3 is suitable for providing an operating mode for tissue sealing that may require a higher output current of, for example, a maximum of 10 A, but not quite as high an output voltage of, for example, 440 V.

In the exemplary embodiment shown in FIG. 3, however, the outputs for the second working electrode AE2 and the second neutral electrode NE2 are separated from the secondary windings 44.1', 44.2' and 44.3', so that as a result only a single output AE1 and NE1 is effective in each case, just like it is also shown in FIGS. 1 and 2.

If a second operating mode requires a higher output voltage but not such a high output current, the high-frequency parts 16.1 and 16.2 connected in series can be connected with a parallel connection of the primary windings 42.1', 42.2' and 42.3', as shown in FIG. 4. Here, too, the switch S1.2 assigned to the center tap between the two high-frequency parts 16.1 and 16.2 remains completely open. With regard to the primary windings 42.1', 42.2' and 42.3', the switches S2.1 and S2.2 corresponding to the switches S1 and S2 in the exemplary embodiment according to FIG. 2 for connecting the primary windings 42.1', 42.2' and 42.3' in parallel are closed. Due to the fact that the switch S2.1' is connected in parallel to the primary windings 42.1' and 42.2' and the switch S2.2' is connected in parallel to the primary windings 42.2' and 42.3', while at the same time the center primary winding 42.2' is inverted with respect to the two remaining primary windings 42.1' and 42.3', the overall result is the parallel connection of the primary windings 42.1', 42.2' and 42.3' shown at the top left in the equivalent circuit diagram. On the secondary side, in the exemplary embodiment shown in FIG. 4, the secondary windings 44.1', 44.2' and 44.3' are connected in series because the switches S4.1' and S4.2' are closed, and the switches S5.1 and S5.2 are open. Switches S5.1 and S5.2 can be used to connect the secondary windings in 44.1', 44.2' and 44.3' in parallel, as shown in FIG. 3. However, this is not the case in the exemplary embodiment in FIG. 4.

In the exemplary embodiment in FIG. 4, the output voltage is also only provided at outputs for a first working electrode AE1 and a first neutral electrode NE1. The outputs for the second working electrode AE2 and the second neutral electrode NE2 are separated from the secondary windings 44.1', 44.2' and 44.3' by appropriate switches (see switches S6.1, S6.2, S6.3, S6.4, S6.5, S6.6 and S6.7).

In the exemplary embodiment shown in FIG. 4, with a transmission ratio of 1:2 each for the first two individual transformers with their primary windings 42.1' and 42.2' and their secondary windings 44.1' and 44.2', and with a transmission ratio of 1:4 for the third individual transformer with its primary winding 42.3' and its secondary winding 44.3', the total transmission ratio is 1:8 if the primary windings 42.1', 42.2' and 42.3' are connected in parallel and the secondary windings 44.1', 44.2' and 44.3' are connected in series.

The operating modes and configurations shown in FIGS. 3 and 4 can also be provided with the embodiment of an output transformer shown in FIG. 2.

Due to the fact that, in the output transformer shown in FIGS. 3 to 7, two high-frequency parts 16.1 and 16.2 and the corresponding switches S1.1, S1.2 and S1.3 are provided, and the switches S6.1, S6.2, S6.3, S6.4, S6.5, S6.6 and S6.7 are also provided at the output of the output transformer for connecting the terminals of the secondary windings 44.1', 44.2' and 44.3' with the first and, if necessary, also the second working electrode AE1 and AE2 as well as with the first neutral electrode NE1 and, if necessary, also the second neutral electrode NE2, the output transformer according to FIGS. 3 to 7 can also be used to provide further operating modes which cannot be provided with the output transformer according to FIG. 2. This is shown in FIGS. 5, 6, and 7, which illustrate the switch configurations for the other modes of operation.

The output transformer configurations shown in FIGS. 5, 6, and 7 each allow for the connection of two electrosurgical instruments for simultaneous operation. A first electrosurgical instrument is then connected to the first working electrode terminal AE1 and the first neutral electrode terminal NE1, while the second electrosurgical instrument is connected to the second working electrode terminal AE2 and the second neutral electrode terminal NE2.

FIG. 5 shows a configuration of the output transformer in which power is supplied to a first electrosurgical instrument through the terminals AE1 and NE1 of the first high-frequency part 16.1 via the primary windings 42.1' and 42.2' and the secondary windings 44.1' and 44.2', while power to a second instrument connected to the terminal for the second working electrode AE2 and the terminal for the second neutral electrode NE2 is supplied by the second high-frequency part 16.2 via the third primary winding 42.3' and the third secondary winding 44.3'. The third individual transformer thus actually functions as a single transformer, so that its transmission ratio of 1:4 is directly effective. With respect to the remaining primary windings 42.1' and 42.2' and the remaining secondary windings 44.1' and 44.2', the following applies: The primary windings 44.1' and 44.2' are connected in parallel by the closed switch S2.1' and are supplied with power by the first high-frequency part 16.1 when the switches S1.1' and S1.2' are in the corresponding position. The associated secondary windings 44.1' and 44.2', on the other hand, are connected in series because switch S4.1 is closed and switch S5.1 is open. The secondary windings 44.1' and 44.2' are separated from the third secondary winding 44.3' due to the open switches S4.2' and S5.2'. By connecting the primary windings 42.1' and 42.2' in parallel and the associated secondary windings 44.1' and 44.2' connected in series, a total transmission ratio of also 1:4 is obtained, so that with identical high-frequency parts 16.1 and 16.2, the two electrosurgical instruments connected to the terminal for the first working electrode AE1 and the terminal for the first neutral electrode NE1 and, respectively, to the terminal for the second working electrode AE2 and the terminal for the second neutral electrode NE2 are supplied with the same output voltage and can also deliver the same maximum current.

FIG. 6 shows a configuration in which only the first two individual transformers with their primary windings 42.1' and 42.2' and the first two secondary windings 44.1' and 44.2' are used, while the third individual transformer with its third primary winding 42.3' and third secondary winding 44.3' is not used. In the configuration shown in FIG. 6, the first primary winding 42.1' is powered by the first high-frequency part 16.1', while the second primary winding 42.2' is powered by the second high-frequency part 16.2'. The two switches S2.1 and S2.2 are open, and the switch S1.2 connected to the center tap between the two high-frequency parts 16.1 and 16.2 is in a switch position which connects the center tap between the two high-frequency parts 16.1 and 16.2 to a center tap between the two primary windings 42.1' and 42.2'. The two secondary windings 44.1' and 44.2' each function individually because the switches S4.1 and S5.1 are open.

The two switches S4.2 and S5.2 are open just like the switches S6.5, S6.6 and S6.7, so that the third secondary winding 44.3' is galvanically isolated from the remaining components of the transformer and also from the remaining terminals of the output transformer.

In the exemplary embodiment shown in FIG. 6, the first individual transformer with its primary winding 42.1' and its secondary winding 44.1' and the second individual transformer with its primary winding 42.2' and its secondary winding 44.2' thus function independently of each other. The first individual transformer with its primary winding 42.1' and its secondary winding 44.1' supplies voltage to the terminals for the first working electrode AE1 and for the first neutral electrode NE1, while the second individual transformer with its primary winding 42.2' and its secondary winding 44.2' supplies voltage to the terminals for the second working electrode AE2 and the second neutral electrode NE2. Both individual transformers have the same transmission ratio of 1:2, so that the two electrosurgical instruments connected to the first working electrode AE1 and the first neutral electrode NE1 or the second working electrode AE2 and the second neutral electrode NE2 are each supplied with the same voltage again.

Finally, FIG. 7 shows a configuration of the output transformer shown in FIGS. 3 to 7, in which two electrosurgical instruments connected to the terminal for the first working electrode AE1 and the terminal for the first neutral electrode NE1, or to the terminal for the second working electrode AE2 and the terminal for the second neutral electrode NE2, are supplied with different voltages. Specifically, a first electrosurgical instrument connected to the terminal for the first working electrode AE1 and the terminal for the first neutral electrode NE2 is supplied with voltage by the first high-frequency part 16.1 via a series connection of the first and second primary windings 42.1' and 42.2' and a parallel connection of the associated secondary windings 44.1' and 44.2'. On the other hand, a second ultrasound instrument connected to the terminals for the second working electrode AE2 and the second neutral electrode NE2 is supplied with voltage by the second high-frequency part 16.2 with the third individual transformer with its primary winding 42.3' and its secondary winding 44.3'. Since the switches S4.2 and S5.2 are open in this configuration, the third secondary winding 44.3' is separated from the two remaining secondary windings 44.1' and 44.2' so that the third individual transformer functions independently of the two remaining individual transformers as a result.

Regarding the connections for the first working electrode AE1 and the first neutral electrode NE1, they are supplied by the first high-frequency part 16.1 and the series connection of the first and second primary windings 42.1' and 42.2' as well as the parallel connection of the associated secondary windings 44.1' and 44.2' in that the switch S2.1 is open on the primary side (the switch S2.2 is also open in order to isolate the third primary winding 42.3' from the remaining primary windings 42.1' and 42.2), and the two switches S4.1 and S5.1 are closed on the secondary side.

The switch positions shown in FIG. 7 result in a configuration of the output transformer that is again shown in the top left of FIG. 7 in the form of an equivalent circuit diagram. This diagram shows that, in this case, the electrosurgical instrument connected to the terminal for the first working electrode AE1 and the terminal for the first neutral electrode NE1 is supplied with a voltage of 275 V and can deliver a maximum current of 8 A. These are exactly the output values of the first high-frequency part 16.1, since the transformer formed by the first individual transformers has an overall transmission ratio of 1:1 due to the identical transmission ratios of the first two individual transformers of 1:2 as well as the series connection of the primary windings 42.1' and 42.2' as well as the parallel connection of the associated secondary windings 44.1' and 44.2'.

Due to the transmission ratio of 1:4, the electrosurgical instrument connected to the terminals for the second working electrode AE2 and the second neutral electrode NE2 is supplied with four times the output voltage of the second high-frequency part 16.2, i.e. 1100 V in the example.

An electrosurgical generator with this type of output transformer makes it possible to avoid such disadvantages of the prior art that are due to the fact that, in transformers with different taps (instead of individual transformers), the unused turns also carry voltage because they are magnetically linked to the remaining turns. These voltages put a lot of strain on the dielectric between the turns and can cause leakage current to the patient. In addition, a transformer with multiple taps is complex.

The disadvantage of providing different individual output transformers instead of one switchable output transformer is that it requires more space, more material and more switches than the solution proposed according to the invention. Also, a solution with different output transformers is not efficient if only because only one of the output transformers is always in operation.

LIST OF REFERENCE NUMBERS

10 Electrosurgical generator
12 High-voltage power supply
14 Output
16 High-frequency part
20.1, 20.2 Outputs
40.1, 40.2, 40.3 Output transformers
42.1, 42.2, 42.3 Primary windings
44.1, 44.2, 44.3 Secondary windings
46 Control unit

The invention claimed is:

1. Electrosurgical generator for providing different high-frequency alternating voltages/high-frequency currents, comprising at least two outputs to which an electrosurgical instrument is or can be connected, at least one high-frequency voltage source, and at least two output transformers each having at least one primary winding and one secondary winding, wherein the output transformers are configured to each be selectively connected on the primary side to the high-frequency voltage source and on the secondary side to the outputs for an electrosurgical instrument,
wherein the electrosurgical generator comprises switching means, by which:
the primary windings of the output transformers are configured to each be selectively connected in parallel and/or in series or operated individually as well as the secondary windings of the output transformers are configured to each be selectively connected in parallel and/or in series or operated individually.

2. Electrosurgical generator according to claim 1, wherein at least one output transformer has at least one tap on the primary and/or secondary side.

3. Electrosurgical generator according to claim 1, wherein the outputs of the secondary windings of the output transformers can be connected via switching means to the outputs for an electrosurgical instrument.

4. Electrosurgical generator according to claim 1, wherein the activation of the switches is performed via a control unit.

5. Electrosurgical generator according to claim 1, wherein, for setting four different transmission ratios between the high-frequency voltage source and the outputs for an electrosurgical instrument, three output transformers are provided, the windings of which can be connected both on the primary side and on the secondary side via two switches each.

6. Electrosurgical generator according to claim 5, wherein the transmission ratios of the two outer output transformers are configured differently.

7. Electrosurgical generator according to claim 6, wherein the transmission ratio of the center output transformer is identical to the smaller transmission ratio of the outer output transformers.

8. Electrosurgical generator according to claim 1, wherein the electrosurgical generator comprises at least two high-frequency voltage sources.

9. Electrosurgical generator according to claim 8, wherein the voltage sources can be connected via switches to the primary windings of the output transformers.

10. Electrosurgical generator according to claim 1, wherein the switches are relays.

11. Electrosurgical generator according to claim 1 that is configured to provide an AC output voltage at a frequency between 0.2 MHz and 3 MHz at its outputs.

12. Electrosurgical generator according to claim 1 that is configured to provide an AC output voltage between 200 V and 5 kV at its outputs.

13. Electrosurgical generator according to claim 1 that is configured to provide an output power of up to 500 W at its outputs.

* * * * *